US012672847B2

(12) United States Patent
Corrigan et al.

(10) Patent No.: US 12,672,847 B2
(45) Date of Patent: Jul. 7, 2026

(54) SYSTEMS, CATHETERS, DRIVE UNITS, AND METHODS FOR AUTOMATIC CATHETER IDENTIFICATION

(71) Applicant: Boston Scientific Scimed, Inc., Maple Grove, MN (US)

(72) Inventors: Joe Corrigan, Cambridge (GB); Peter Thornton, Jr., Los Altos, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/916,904

(22) Filed: Oct. 16, 2024

(65) Prior Publication Data
US 2025/0032089 A1 Jan. 30, 2025

Related U.S. Application Data

(63) Continuation of application No. 16/165,422, filed on Oct. 19, 2018, now abandoned.

(51) Int. Cl.
| | |
|---|---|
| *A61B 8/00* | (2006.01) |
| *A61B 8/12* | (2006.01) |
| *A61B 90/90* | (2016.01) |
| *A61B 90/94* | (2016.01) |
| *A61B 90/96* | (2016.01) |

(52) U.S. Cl.
CPC ............. *A61B 8/4438* (2013.01); *A61B 8/12* (2013.01); *A61B 8/445* (2013.01); *A61B 8/4461* (2013.01); *A61B 90/90* (2016.02); *A61B 90/94* (2016.02); *A61B 90/96* (2016.02)

(58) Field of Classification Search
CPC ......... A61B 8/4438; A61B 8/12; A61B 8/445; A61B 8/4461; A61B 90/90; A61B 90/94; A61B 90/96; A61B 8/54; A61B 8/56; A61B 8/0891
See application file for complete search history.

(56) References Cited

U.S. PATENT DOCUMENTS

| | | | |
|---|---|---|---|
| 4,841,977 | A | 6/1989 | Griffith et al. |
| 5,375,602 | A | 12/1994 | Lancee et al. |
| 6,370,411 | B1 | 4/2002 | Osadchy et al. |
| 6,945,938 | B2 | 9/2005 | Grunwald |
| 7,037,271 | B2 | 5/2006 | Crowley |
| 7,246,959 | B2 | 7/2007 | Nakatani |
| 7,306,561 | B2 | 12/2007 | Sathyanarayana |
| 7,622,853 | B2 | 11/2009 | Rehrig et al. |
| 8,523,778 | B2 | 9/2013 | Sadaka |

(Continued)

FOREIGN PATENT DOCUMENTS

| | | |
|---|---|---|
| CN | 104246790 A | 12/2014 |
| CN | 105749431 A | 7/2016 |

(Continued)

*Primary Examiner* — Michael J Carey
*Assistant Examiner* — Zainab Mohammed Aldarraji
(74) *Attorney, Agent, or Firm* — Seager, Tufte & Wickhem, LLP

(57) ABSTRACT

A catheter for an ultrasound system can a marker disposed on the hub. The marker is optically or magnetically readable and, when read, identifies the catheter. A drive unit can include an optical or magnetic marker reader. Alternatively or additionally, a catheter may include an active memory arrangement that can be read by an appropriate reader on the drive unit.

19 Claims, 7 Drawing Sheets

(56) References Cited

U.S. PATENT DOCUMENTS

| | | | |
|---|---|---|---|
| 10,628,937 B2 | 4/2020 | Shu et al. | |
| 2004/0108789 A1 | 6/2004 | Marshall | |
| 2004/0171935 A1 | 9/2004 | Van Creveld et al. | |
| 2006/0058622 A1 | 3/2006 | Tearney et al. | |
| 2006/0084875 A1 | 4/2006 | Knight | |
| 2006/0100522 A1 | 5/2006 | Yuan et al. | |
| 2006/0106320 A1 | 5/2006 | Barbato | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |
| 2007/0083111 A1 | 4/2007 | Hossack et al. | |
| 2007/0083119 A1 | 4/2007 | Adachi et al. | |
| 2009/0163817 A1 | 6/2009 | Masters et al. | |
| 2009/0264769 A1 | 10/2009 | Sadaka | |
| 2009/0270737 A1 | 10/2009 | Thornton | |
| 2010/0249603 A1 | 9/2010 | Hastings et al. | |
| 2011/0071400 A1 | 3/2011 | Hastings et al. | |
| 2011/0098573 A1 | 4/2011 | Thornton et al. | |
| 2011/0125027 A1* | 5/2011 | Sadaka | A61B 8/14 600/467 |
| 2011/0207995 A1 | 8/2011 | Snow et al. | |
| 2012/0253197 A1 | 10/2012 | Sadaka | |
| 2013/0079642 A1 | 3/2013 | Marshall et al. | |
| 2014/0187965 A1* | 7/2014 | Reiter | A61B 8/445 600/467 |
| 2016/0166328 A1* | 6/2016 | De Vries | A61B 90/30 600/7 |
| 2017/0165454 A1 | 6/2017 | Tuohy et al. | |
| 2018/0264227 A1 | 9/2018 | Flexman et al. | |
| 2020/0405311 A1 | 12/2020 | Shelton, IV et al. | |

FOREIGN PATENT DOCUMENTS

| | | |
|---|---|---|
| CN | 107752985 A | 3/2018 |
| CN | 108290027 A | 7/2018 |
| EP | 2679167 A1 | 1/2014 |
| EP | 2832295 A1 | 2/2015 |
| JP | 2005177205 A | 7/2005 |
| JP | 20110152274 A | 8/2011 |
| WO | 2009048339 A1 | 4/2009 |
| WO | 2009073752 A1 | 6/2009 |
| WO | 2009121067 A1 | 10/2009 |

* cited by examiner

*104*

Display(s) — *112*

Processor — *106*

*110*

Drive Unit

Pulse Generator — *108*

*100*

*102*

SYSTEMS, CATHETERS, DRIVE UNITS, AND METHODS FOR AUTOMATIC CATHETER IDENTIFICATION

CROSS-REFERENCE TO RELATED APPLICATIONS

This application is a continuation of U.S. application Ser. No. 16/165,422, filed Oct. 19, 2018, the entire disclosure of which is hereby incorporated by reference.

TECHNICAL FIELD

The present disclosure is directed to the area of intravascular ultrasound imaging systems and methods of making and using the systems. The present disclosure is also directed to intravascular ultrasound imaging systems that include arrangements for automatic catheter identification when the catheter is attached to a drive unit.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include a control module (with a pulse generator, an image processor, and a monitor), a drive unit, a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic signals that are transmitted through patient tissue. Reflected pulses of the transmitted acoustic signals are absorbed by the one or more transducers and transformed to electric pulses. The transformed electric pulses are delivered to the image processor and converted to an image displayable on the monitor.

BRIEF SUMMARY

One aspect is a catheter for an ultrasound system that includes a catheter sheath defining a lumen; a hub coupled to the catheter sheath and configured for attachment to a motor drive; an elongated, rotatable driveshaft disposed within the lumen of the catheter sheath and extending into the hub, the driveshaft having a proximal end and a distal end, wherein the proximal end is configured and arranged for coupling to the motor drive for rotating the driveshaft; an imaging device coupled to the distal end of the driveshaft with rotation of the driveshaft causing a corresponding rotation of the imaging device, the imaging device including at least one transducer configured and arranged for transforming applied electrical signals to acoustic signals and also for transforming received echo signals to electrical signals; at least one conductor extending from the hub through the lumen of the catheter sheath and coupled to the imaging device for carrying the electrical signals; and a marker disposed on the hub, wherein the marker is optically or magnetically readable and, when read, identifies the catheter.

In at least some aspects, the marker is optically readable. In at least some aspects, the marker includes a one- or two-dimensional code. In at least some aspects, the marker includes a barcode or QR code.

In at least some aspects, the marker is magnetically readable. In at least some aspects, the marker includes a strip with information magnetically encoded thereon.

In at least some aspects, the marker is printed onto the hub. In at least some aspects, the marker is adhered to the catheter with an adhesive. In at least some aspects, the marker is disposed on a rotating portion of the hub.

In at least some aspects, the marker, when read, identifies a type of the catheter. In at least some aspects, the marker, when read, identifies a serial number of the catheter. In at least some aspects, the marker, when read, identifies an expiration date of the catheter.

In at least some aspects, the marker extends around a full circumference of the hub. In at least some aspects, the marker is disposed on non-curved surface of the hub.

Another aspect is an ultrasound system that includes any of the catheters described above; and a drive unit coupleable to the catheter. The drive unit includes a drive hub configured for attachment to the hub of the catheter; a rotation mechanism configured for rotating the driveshaft of the catheter; and a marker reader configured to optically or magnetically read the marker on the catheter to identify the catheter.

In at least some aspects, the ultrasound system further includes a processor coupleable to the drive unit and configured for identifying the catheter from the marker when read by the marker reader. In at least some aspects, the processor is further configured for altering or setting one or more settings of the ultrasound system in response to the identification of the catheter.

Another aspect is a drive unit for an ultrasound system that includes a drive hub configured for attachment to a catheter; a rotation mechanism configured for rotating a driveshaft of the catheter; and a reader configured to optically or magnetically read a marker on the catheter to identify the catheter.

In at least some aspects, the reader is an optical reader. In at least some aspects, the reader is a magnetic reader.

Yet another aspect is a catheter for an ultrasound system that includes a catheter sheath defining a lumen; a hub coupled to the catheter sheath and configured for attachment to a motor drive; an elongated, rotatable driveshaft disposed within the lumen of the catheter sheath and extending into the hub, the driveshaft having a proximal end and a distal end, wherein the proximal end is configured and arranged for coupling to the motor drive for rotating the driveshaft; an imaging device coupled to the distal end of the driveshaft with rotation of the driveshaft causing a corresponding rotation of the imaging device, the imaging device including at least one transducer configured and arranged for transforming applied electrical signals to acoustic signals and also for transforming received echo signals to electrical signals; at least one conductor extending from the hub through the lumen of the catheter sheath and coupled to the imaging device for carrying the electrical signals; and an active memory arrangement disposed on the hub, wherein the active memory arrangement is configured for transferring information using a single conductor and is configured to store information that identifies the catheter.

Another aspect is an ultrasound system that includes any of the catheters described above; and a drive unit coupleable to the catheter. The drive unit includes a drive hub configured for attachment to the hub of the catheter; a rotation mechanism configured for rotating the driveshaft of the catheter; and a reader configured to obtain the information from the active memory arrangement on the catheter to identify the catheter.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of intravascular ultrasound imaging systems and methods of making and using the systems. The present disclosure is also directed to intravascular ultrasound imaging systems that include arrangements for automatic catheter identification when the catheter is attached to a drive unit.

Suitable intravascular ultrasound ("IVUS") imaging systems include, but are not limited to, one or more transducers disposed on a distal portion of a catheter configured and arranged for percutaneous insertion into a patient. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated herein by reference.

Figure 1:
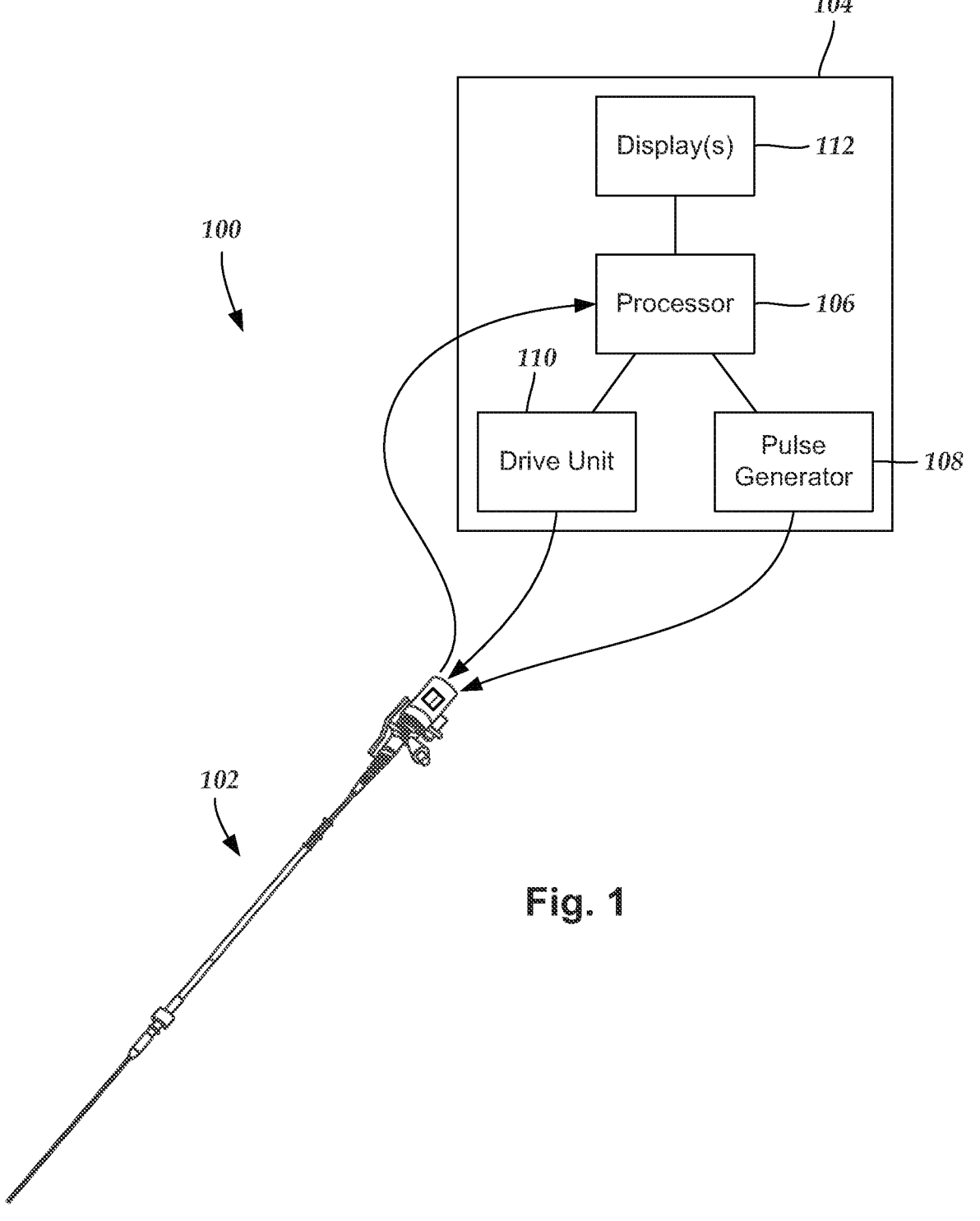
FIG. 1 is a schematic view of one embodiment of an intravascular ultrasound imaging system.

FIG. 1 schematically shows one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric signals that are input to one or more transducers (312 in FIG. 3) disposed in the catheter 102. In at least some embodiments, electric signals transmitted from the one or more transducers (312 in FIG. 3) is input to the processor 106 for processing. The processed electric signals from the one or more transducers (312 in FIG. 3) may be displayed as one or more images on the one or more displays 112. In at least some embodiments, mechanical energy from the drive unit 110 is used to drive an imaging core (306 in FIG. 3) disposed in the catheter 102. For example, the drive unit 110 can be used to rotate the imaging core or to pullback the imaging core along vasculature of the patient or any combination thereof. In at least some embodiments, the drive unit 110 is spatially separated from the other components of the control module 104 and may be coupled to the processor using a cord or other wired arrangement or by wireless connection.

The processor 106 may also be used to control the functioning of one or more of the other components of the control module 104. For example, the processor 106 may be used to control at least one of the frequency or duration of the electrical signals transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
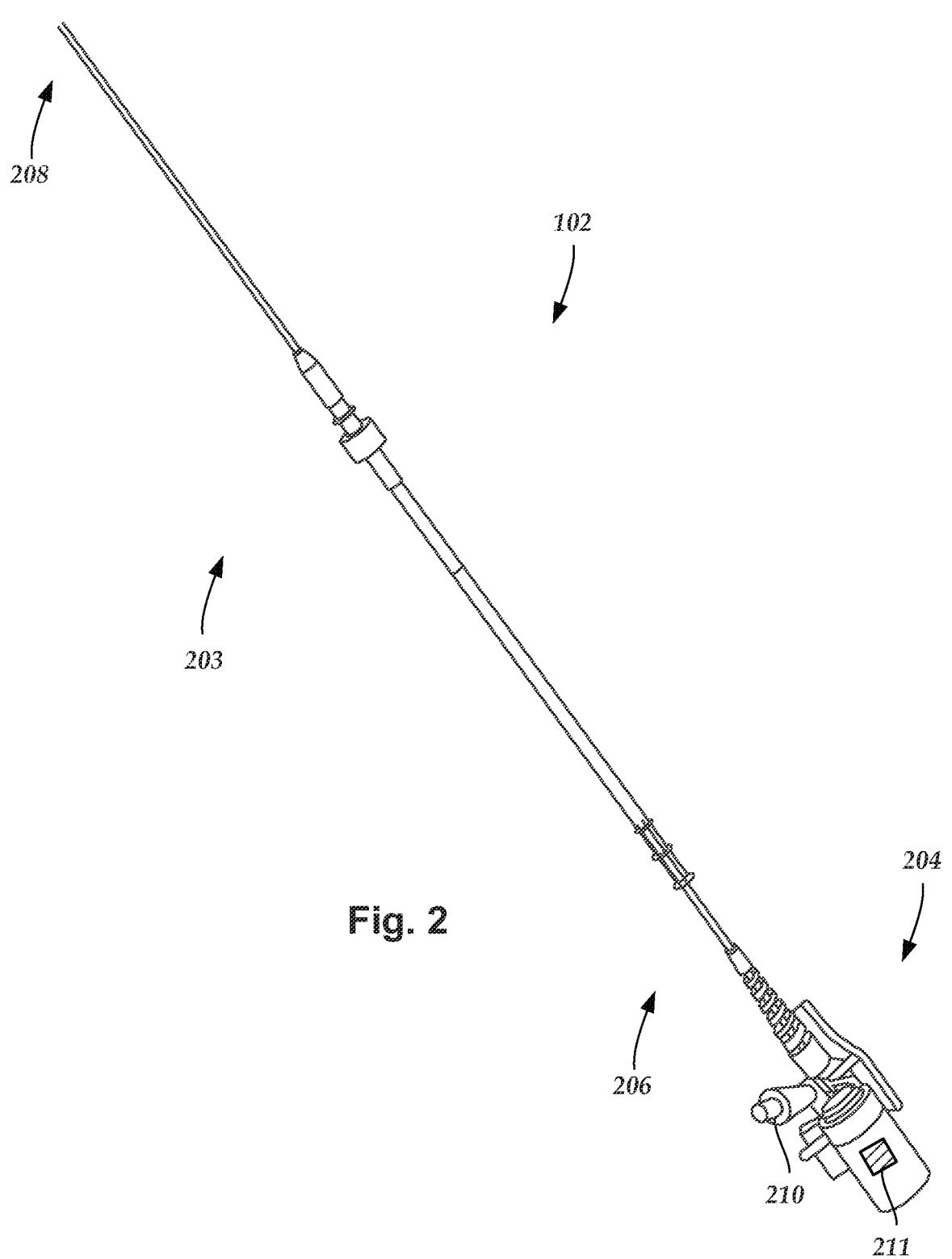
FIG. 2 is a schematic side view of one embodiment of a catheter of an intravascular ultrasound imaging system.

FIG. 2 shows, in schematic side view, one embodiment of the catheter 102 of the IVUS imaging system (100 in FIG. 1). The catheter 102 includes an elongated member 203 and a hub 204. The elongated member 203 includes a proximal portion 206 and a distal portion 208. In FIG. 2, the proximal portion 206 of the elongated member 203 is coupled to the catheter hub 204 and the distal portion 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the drive unit (110 in FIG. 1). In some embodiments, the elongated member 203 and the hub 204 are formed as a unitary body. In other embodiments, the elongated member 203 and the hub 204 are formed separately and subsequently assembled together. In addition, as described in more detail below, the catheter 102 can also include a marker 211 which, when read, can identify the catheter. For example, the marker 211 can identify the type of the catheter (using, for example, an identification code or a name or any other suitable identification information) or can include a serial number for the catheter or any other catheter identification information or any combination thereof.

Figure 3:
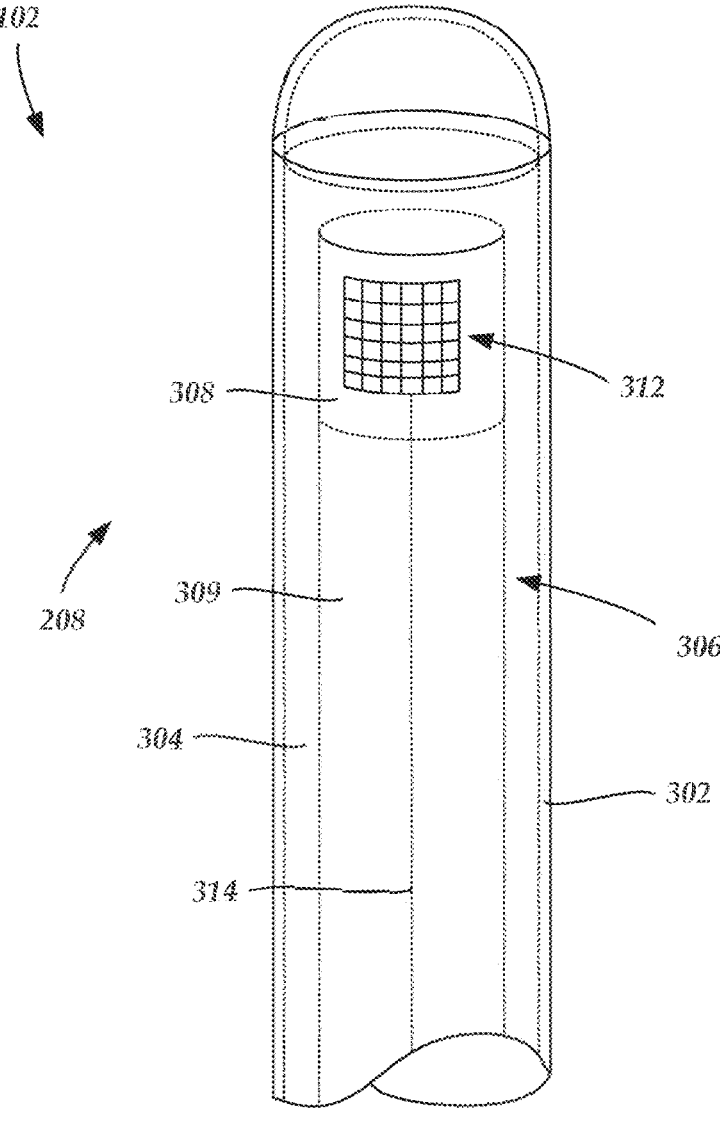
FIG. 3 is a schematic perspective view of one embodiment of a distal end of the catheter shown in FIG. 2 with an imaging core disposed in a lumen defined in the catheter.

FIG. 3 shows, in schematic perspective view, one embodiment of the distal portion 208 of the elongated member 203 of the catheter 102. The elongated member 203 includes a sheath 302 and a lumen 304. An imaging core 306 is disposed in the lumen 304. The imaging core 306 includes an imaging device housing 308 coupled to a distal end of a transducer connection system, such as a drive cable or driveshaft 309.

The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device housing 308 and employed to transmit and receive acoustic signals. In a preferred embodiment (as shown in FIG. 3), an array of transducers 312 are mounted to the imaging device housing 308. In other embodiments, a single transducer may be employed. In yet other embodiments, multiple transducers in an irregular-array may be employed. Any number of transducers 312 can be used. For example, there can be one, two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical signals to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic signals of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic signals of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic signals.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one or more transducers 312 may be used to form an image of the walls of the blood vessel and tissue surrounding the blood vessel.

In at least some embodiments, the imaging core 306 is rotated about a longitudinal axis of the catheter 102. As the imaging core 306 rotates, the one or more transducers 312 emit acoustic signals in different radial directions. When an emitted acoustic signal with sufficient energy encounters one or more medium boundaries, such as one or more tissue boundaries, a portion of the emitted acoustic signal is reflected back to the emitting transducer as an echo signal. Each echo signal that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic signals transmitted and the echo signals received. In at least some embodiments, the rotation of the imaging core 306 is driven by the drive unit 110 (FIG. 1).

As the one or more transducers 312 rotate about the longitudinal axis of the catheter 102 emitting acoustic signals, multiple images are formed that collectively form a radial cross-sectional image of a portion of the region surrounding the one or more transducers 312, such as the walls of a blood vessel of interest and the tissue surrounding the blood vessel. In at least some embodiments, the radial cross-sectional image can be displayed on one or more displays 112.

In at least some embodiments, the imaging core 306 may also move axially along the blood vessel within which the catheter 102 is inserted so that a plurality of cross-sectional images may be formed along an axial length of the blood vessel. In at least some embodiments, during an imaging procedure the one or more transducers 312 are retracted (i.e., pulled back) along the longitudinal length of the catheter 102. In at least some embodiments, the catheter 102 includes at least one telescoping section that can be retracted during pullback of the one or more transducers 312. In at least some embodiments, the drive unit 110 drives the pullback of the imaging core 306 within the catheter 102. In at least some embodiments, the drive unit 110 pullback distance of the imaging core is at least 5 cm. In at least some embodiments, the drive unit 110 pullback distance of the imaging core is at least 10 cm. In at least some embodiments, the drive unit 110 pullback distance of the imaging core is at least 15 cm. In at least some embodiments, the drive unit 110 pullback distance of the imaging core is at least 20 cm. In at least some embodiments, the drive unit 110 pullback distance of the imaging core is at least 25 cm.

The quality of an image produced at different depths from the one or more transducers 312 may be affected by one or more factors including, for example, bandwidth, transducer focus, beam pattern, as well as the frequency of the acoustic signal. The frequency of the acoustic signal output from the one or more transducers 312 may also affect the penetration depth of the acoustic signal output from the one or more transducers 312. In general, as the frequency of an acoustic signal is lowered, the depth of the penetration of the acoustic signal within patient tissue increases. In at least some embodiments, the IVUS imaging system 100 transmits acoustic signals centered at an operational frequency. The operational frequency is typically within a range of 5 MHz to 60 MHz. The acoustic signals may be transmitted within a frequency bandwidth that includes the operational frequency.

In at least some embodiments, the one or more transducers 312 may be mounted to the distal portion 208 of the imaging core 306. The imaging core 306 may be inserted in the lumen of the catheter 102. In at least some embodiments, the catheter 102 (and imaging core 306) are inserted percutaneously into a patient via an accessible blood vessel, such as the femoral artery, at a site remote from a target imaging location. The catheter 102 may then be advanced through patient vasculature to the target imaging location, such as a portion of a selected blood vessel.

As discussed above, the driveshaft 309 couples the imaging device housing 308 to the drive unit (110 in FIG. 1). In at least some embodiments, one or more transducer conductors 314 electrically couple the one or more transducers 312 to the control module (104 in FIG. 1).

Figure 4A:
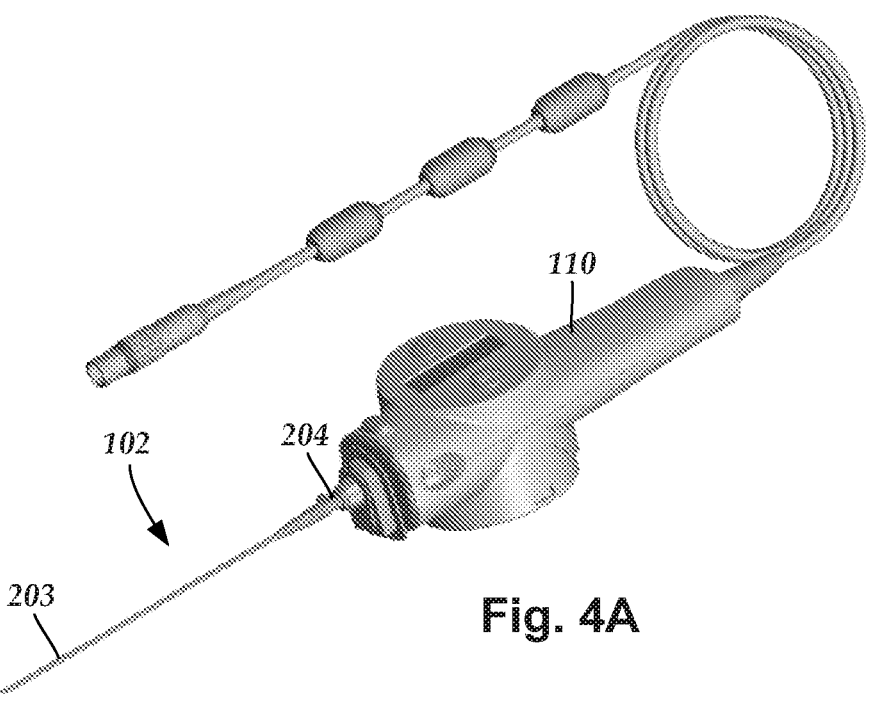
FIG. 4A is a schematic perspective view of one embodiment of a catheter coupled to a drive unit of an intravascular ultrasound imaging system.

FIG. 4A shows, in perspective view, one embodiment of a catheter 102 coupled to a drive unit 110. The catheter 102 includes an elongated member 203 (e.g., catheter sheath) and a hub 204. As shown in FIG. 4A, the hub 204 of the catheter 102 is coupled to the drive unit 110 with the elongated member 203 extending outward from the drive unit 110. As described above, the drive unit 110 can be coupled to one or more other components of an IVUS imaging system, such as a pulse generator, a processor, a display, or the like.

Figure 4B:
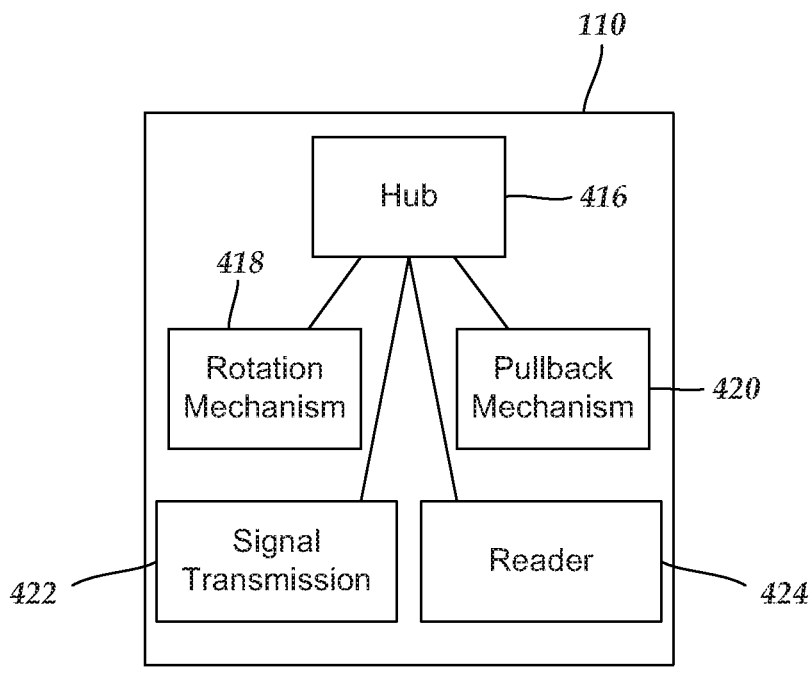
FIG. 4B is a schematic block diagram of one embodiment of a drive unit.

Any suitable drive unit can be used. FIG. 4B is a block diagram illustrating one example of components that can be part of a drive unit 110. It will be recognized that a drive unit may include more or fewer components and may include one or more additional components. In the embodiment of FIG. 4B, the drive unit 110 includes a hub 416 for coupling to the catheter, a rotation mechanism 418 for rotating the driveshaft of the catheter, a pullback mechanism 420 for pulling back the driveshaft of the catheter during the imaging procedure, and a signal transmission unit 422 that conveys signals (drive signals or ultrasound response signals) between the catheter and a pulse generator or processor of the IVUS imaging system. In addition, as described in more detail below, the drive unit 110 can include a reader 424, such as an optical or magnetic reader.

Drive units are typically reusable and can be compatible with a variety of different catheters 102. The different catheters that are compatible with a drive unit may house transducers having different operational frequencies at which the transducers operate or other different operational settings or differences. It is useful if the drive unit 110, and associated processor 106 (FIG. 1), can automatically determine which type of catheter 102 is attached to the drive unit 110.

In one commercial embodiment, the identification of the catheter type includes the catheter having a small printed circuit (PC) board with short, opens, or diodes between three pads on the board. The PC board is connected to the motor drive 110 through spring pins on the PC board (and part of the catheter) that connect it through the motor drive 110 to the processor 106 (FIG. 1) which "reads" the code, identifies the catheter 102, and adjusts settings appropriate to the catheter type. This arrangement, however, may be prone to error arising from contamination of the spring pins or motor drive connector, insufficient travel in the spring pins, or saline contamination of the PC board or motor drive connector creating shorts between the pads that can misinterpreted as the wrong catheter ID code.

Instead of this pin/PC board combination, a marker 211 can be applied to the exterior of the catheter hub, as illustrated in FIG. 2, and can be read or scanned by the system (for example, the drive unit) as the catheter hub 204 is coupled to the drive unit. In at least some embodiments, it may be possible to retrofit existing catheters or drive units to include the marker and reader, respectively. The marker 211 can be used to identify the catheter. For example, the marker 211 can identify the type of the catheter (using, for example, an identification code or a name or any other suitable identification information) or can include a serial number for the catheter or any other catheter identification information or any combination thereof. In at least some embodiments, the ultrasound system can use this identification information for settings for the system or to limit or provide system features based on the identification of the catheter or otherwise use the identification to facilitate operation or use of the catheter.

In at least some embodiments, the marker 211 may also include an expiration date or other shelf-life or expiration information. In at least some embodiments, the system may prevent or limit use or reuse of the catheter or provide a warning to the user regarding the expiration, or any combination of these actions if the expiration date has passed when the catheter is coupled to the drive unit.

Figure 5:
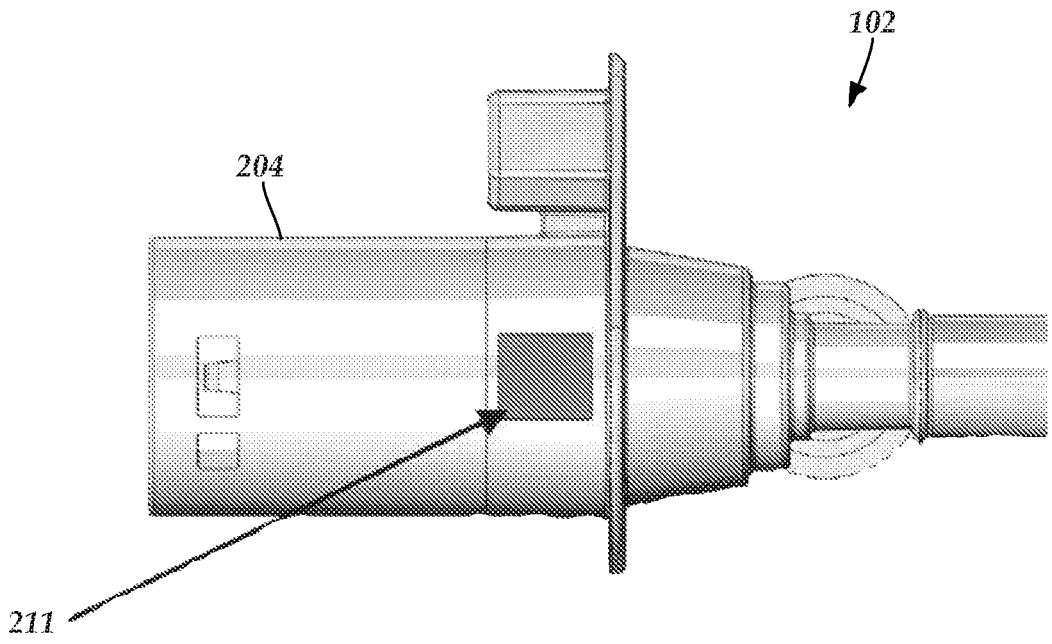
FIG. 5 is a schematic side view of one embodiment of a portion of a catheter with a marker on the hub of the catheter.

FIG. 5 illustrates one embodiment of a marker 211 attached to the hub 204 of a catheter 102. The marker 211 can be, for example, a one-dimension or two-dimensional code that can be optically or magnetically read. For example, the marker 211 can be a barcode, a QR code, or any other suitable code that can be optically read. For example, such a marker 211 could be laser-printed, pad-printed, heat stamped, adhesively adhered, or otherwise attached, inscribed, or positioned onto the hub 204.

Figure 6:
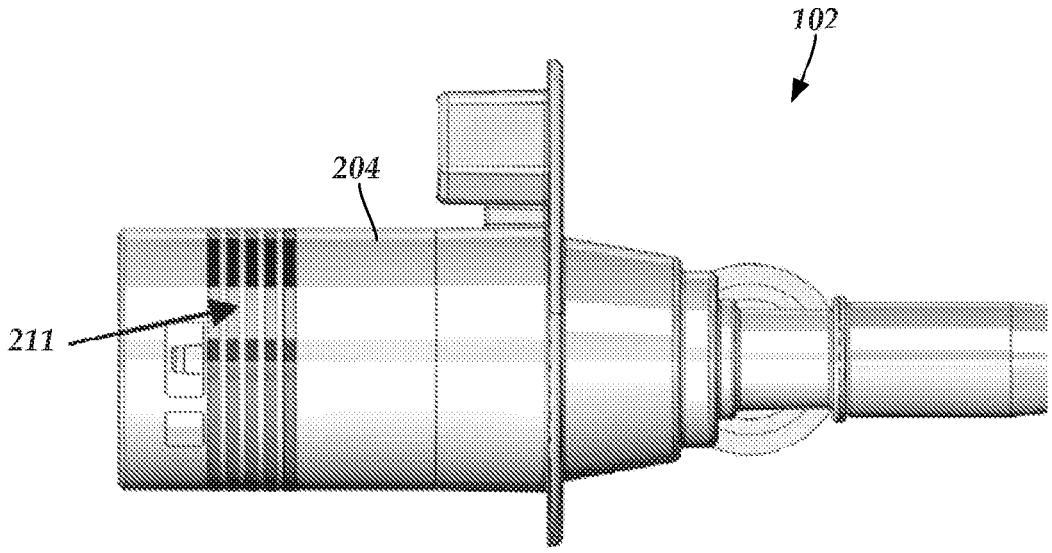
FIG. 6 is a schematic side view of another embodiment of a portion of a catheter with a marker on the hub of the catheter.

FIG. 6 illustrates another embodiment of a marker 211 in the form of multiple circumferential rings (or portions of rings) that can be optically or magnetically read. For example, such a marker 211 could be laser-printed, pad-printed, heat stamped, adhesively adhered, or otherwise attached or inscribed onto the hub 204.

The marker 211 could be a magnetic stripe or any other suitable magnetic marker which can be read magnetically. The magnetic strip can be adhered or otherwise attached to the hub using an adhesive or any other suitable method.

The marker 211 can be a 1-Wire™ memory arrangement (such as those available from Maxim Integrated, San Jose, CA) or other active memory arrangement on which the identification of the catheter is stored. The 1-Wire™ memory arrangement provides for low-speed data transfer over a single conductor using a communication protocol. The corresponding reader in this embodiment would be a reader capable of obtaining information from the 1-Wire™ or other active memory arrangement.

Figure 7:
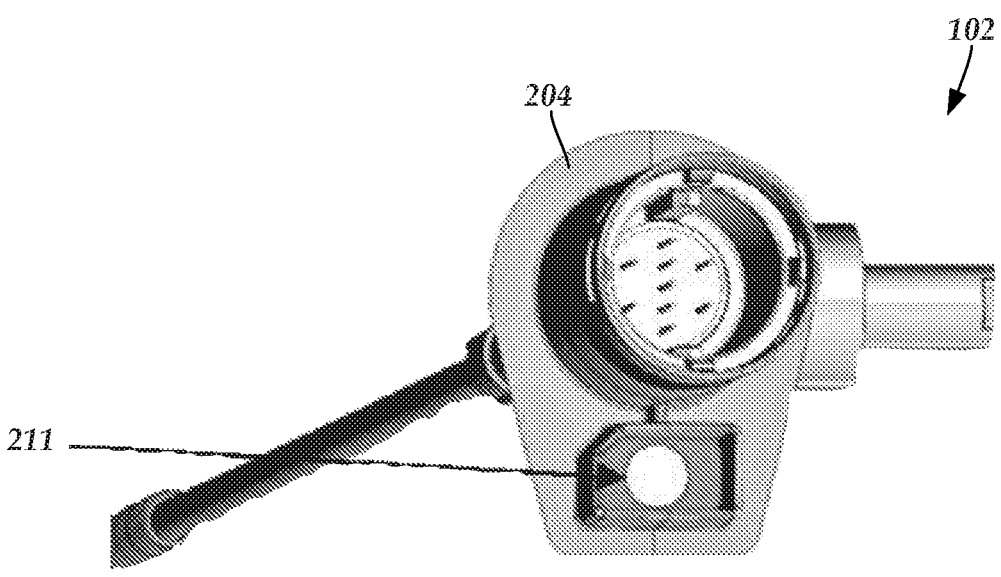
FIG. 7 is a schematic perspective view of a third embodiment of a portion of a catheter with a marker on the hub of the catheter.

FIG. 7 illustrates another embodiment in which the marker 211 is positioned on a flat (e.g., non-curved) surface of the hub 204 of the catheter 102 instead of a cylindrical or curved surface, as illustrated in FIGS. 5 and 6.

Figure 8:
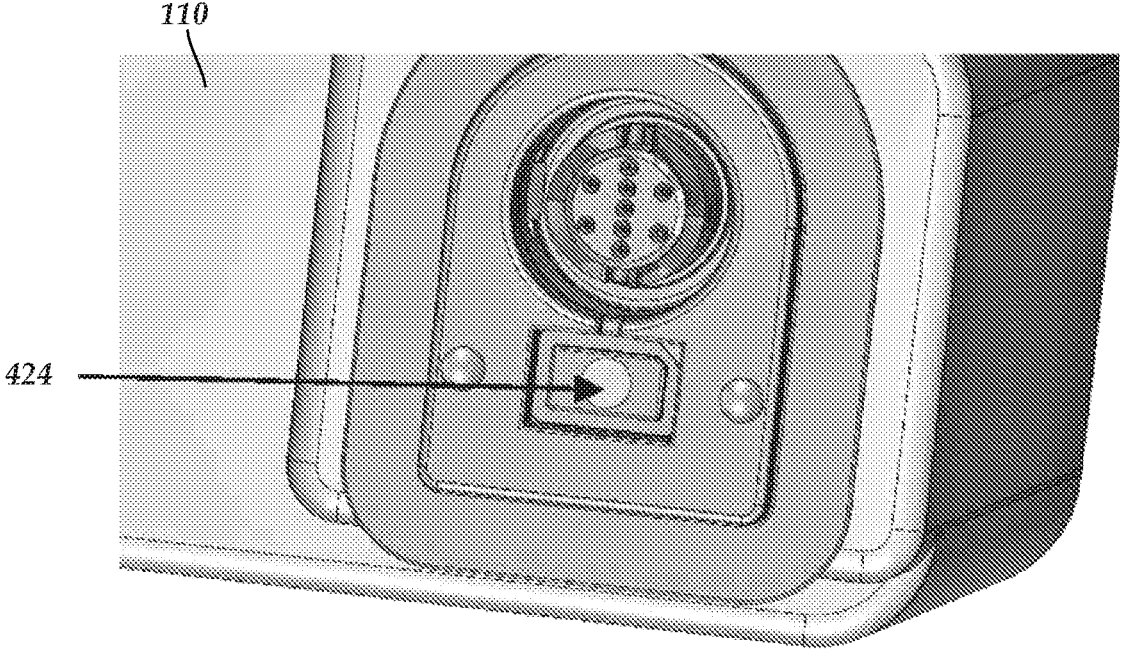
FIG. 8 is a schematic side view of one embodiment of a portion of a drive unit with a marker reader.

FIG. 8 illustrates the drive unit 110 with a corresponding reader 424. The reader can be any suitable optical or magnetic reader including, but not limited to, a camera, a CCD (charge-coupled device) array, magnetic stripe reader, 1-Wire™ or other active memory, or any other suitable reader. In at least some embodiments, the reader 424 of the drive unit 110 may have a processor or memory that can identify the catheter by reading the marker 211 and provide that identification to the processor 106 (FIG. 1) of the control module 104 (FIG. 1). In at least some embodiments, the reader 424 of the drive unit 110 produces signals as the reader 424 reads these markers and these signals are delivered to the processor 106 (FIG. 1) of the control module 104 (FIG. 1) which then identifies the catheter. In at least some embodiments, upon identification of the catheter the processor 106 or other components of the system automatically sets one or more system settings based on the identification of the catheter. In at least some embodiments, the system may limit or provide access to system functions or features based on the identification of the catheter.

In at least some embodiments, fully attaching the hub 204 of the catheter 102 with the drive unit 110 (for example, engaging the drive unit and rotating the hub to a final, locked position) aligns the marker 211 with the reader 424. In at least some embodiments, the hub 204 of the catheter 102 can be inserted or otherwise attached to the drive unit 110 in any orientation and the reader 424 of the drive unit can be arranged to read the marker 211 as the hub of the catheter or drive unit rotates to fully engage. In at least some embodiments, the rotation of the hub 204 of the catheter 102 or drive unit 110 can facilitate reading of the marker 211, such as, for example, reading a bar code.

In at least some embodiments, the reader 424 may be arranged to read the marker 211 regardless of the orientation of the marker relative to the drive unit 110. For example, a barcode or circumferential rings (see, for example, the embodiment illustrated in FIG. 6) may be positioned entirely around a circumference (or at least 50%, 66%, 75%, 80%, 90%, 95% or more of the circumference) to facilitate reading the marker regardless of the orientation of the marker relative to the drive unit. In at least some embodiments, there may be one or more gaps in the barcode or circumferential rings so that the barcode or circumferential rings do not extend entirely around the circumference, but rather includes one or more interruptions (i.e., gaps) around the ring. In at least some embodiments, properly engaging the hub 204 of the catheter 102 with the drive unit 110 (for example, as illustrated in the embodiments illustrated in FIGS. 7 and 8) aligns the marker 211 with the reader 424.

In at least some embodiments, if the marker 211 cannot be read or does not provide the expected information or produces an error, the system may direct the user to disengage and recouple the catheter 102 to the drive unit 110 so that the marker 211 can be reread. The system may alert the user if there are multiples read failures and the user may be requested to manually enter the catheter information.

Figure 9:
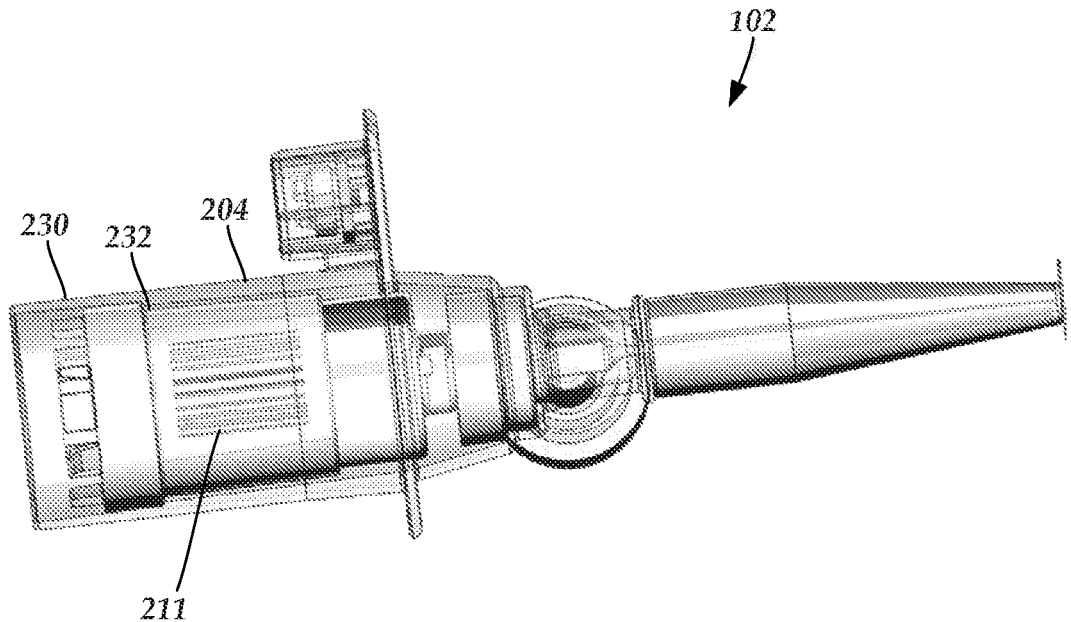
FIG. 9 is a schematic perspective view of a fourth embodiment of a portion of a catheter with a marker on a rotating portion of the hub of the catheter, the housing of the hub in FIG. 9 is partially transparent to illustrate components of the hub within the housing including the rotating portion of the hub and the marker.

In at least some embodiments, the marker 211 can be attached to a rotating portion of the catheter so that the rotational motion can facilitate reading of the marker. FIG. 9 illustrates one embodiment of a hub 204 of a catheter 102 with a housing 230 (which, FIG. 9, is partially transparent in order to view components in the interior of the housing) and a rotating hub portion 232 that couples to the driveshaft 309 (FIG. 3) of the catheter and, when the catheter is coupled to the drive unit 110 (FIG. 4), couples to the rotation mechanism 418 (FIG. 4) of the drive unit. In this embodiment, the reader 424 (FIG. 4) of the drive unit 110 (FIG. 4) is positioned within the drive unit so that the reader 424 can read the marker when the catheter is coupled to the drive unit. In at least some embodiments, the rotation of the rotating hub portion 232 of the catheter 102 during operation or testing of the system can facilitate reading of the marker 211, such as, for example, reading a bar code. For example, the marker 211 can be a one-dimensional bar code that can be read as the rotating hub portion 232 is rotated by the rotation mechanism 418 (FIG. 4) of the drive unit 110 (FIG. 4).

The above specification and examples provide a description of the invention and the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An intravascular imaging device, comprising:
a catheter having a proximal end region;
a hub coupled to the proximal end region, the hub being configured to be secured to a control module that includes a drive unit and a processor;
an imaging core disposed within the catheter, the imaging core including a rotatable drive shaft and an imaging transducer coupled to a distal end of the rotatable drive shaft;
wherein the rotatable drive shaft is configured to be coupled to the drive unit;
a reader coupled to the processor;
a marker coupled to the hub, the marker being configured to identify the catheter when read by the reader; and
a housing disposed on and projecting from the hub in a direction that is parallel to a longitudinal axis of the catheter, the housing being disposed about the marker and being configured to axially align the marker with the reader by engaging and nesting with a projection disposed about the reader.

2. The intravascular imaging device of claim 1, wherein the marker is disposed along a rotatable portion of the hub.

3. The intravascular imaging device of claim 1, wherein the hub includes a flush port.

4. The intravascular imaging device of claim 1, wherein the drive unit includes a rotation mechanism.

5. The intravascular imaging device of claim 1, wherein the drive unit includes a pullback mechanism.

6. The intravascular imaging device of claim 1, wherein the marker includes a one-dimensional or two-dimensional code that can be optically or magnetically read by the reader.

7. The intravascular imaging device of claim 1, wherein the reader includes an optical or magnetic reader.

8. The intravascular imaging device of claim 1, wherein the marker includes a plurality of rings disposed about at least a portion of the hub.

9. The intravascular imaging device of claim 1, wherein the marker includes a magnetic strip.

10. The intravascular imaging device of claim 1, wherein the hub is configured to axially align the marker with the reader.

11. An intravascular imaging system, comprising:
a catheter having a proximal end region;
a hub coupled to the proximal end region;
a control module coupled to the hub, the control module including a drive unit and a processor;
an imaging core disposed within the catheter, the imaging core including a rotatable drive shaft and an ultrasound imaging transducer coupled to a distal end of the rotatable drive shaft;
wherein the rotatable drive shaft is configured to be coupled to the drive unit;
a reader coupled to the processor;
a marker coupled to the hub, the marker being configured to identify the catheter when read by the reader; and
a housing disposed on and projecting from the hub in a direction that is parallel to a longitudinal axis of the catheter, the housing being disposed about the marker and being configured to axially align the marker with the reader by engaging and nesting with a projection disposed about the reader.

12. The intravascular imaging system of claim 11, wherein the marker includes a one-dimensional or two-dimensional code that can be optically or magnetically read by the reader.

13. The intravascular imaging system of claim 11, wherein the reader includes an optical or magnetic reader.

14. The intravascular imaging system of claim 11, wherein the marker includes a plurality of rings disposed about at least a portion of the hub.

15. The intravascular imaging system of claim 11, wherein the marker includes a magnetic strip.

16. The intravascular imaging system of claim 11, wherein the hub includes a flush port.

17. The intravascular imaging system of claim 11, wherein the drive unit includes a rotation mechanism, a pullback mechanism, or both.

18. A catheter for an ultrasound system, the catheter comprising:

a catheter sheath defining a lumen and a longitudinal axis;

a hub coupled to the catheter sheath, the hub including a flanged region with a housing projecting from the flanged region in a direction parallel to the longitudinal axis of the catheter sheath;

a drive unit configured to be attached to the hub;

an imaging core slidable disposed within the catheter sheath, the imaging core include an ultrasound transducer, a drive shaft, and a conductor coupled to the ultrasound transducer and extending toward the drive unit;

an active memory member disposed on the flanged region of the hub and within the housing projecting from the flanged region, wherein the active memory member is configured for transferring information that identifies the catheter; and wherein the housing projecting from the flanged region is configured to axially align with, nest with, and engage a corresponding projection disposed on the drive unit.

19. The catheter of claim 18, wherein the corresponding projection disposed on the drive unit includes a reader for reading the active memory member.

\* \* \* \* \*